US012597091B2

(12) United States Patent
Spiegel et al.

(10) Patent No.: US 12,597,091 B2
(45) Date of Patent: Apr. 7, 2026

(54) COMPUTER-IMPLEMENTED METHOD, APPARATUS, SYSTEM AND COMPUTER PROGRAM FOR CONTROLLING A SIGHTEDNESS IMPAIRMENT OF A SUBJECT

(71) Applicant: ESSILOR INTERNATIONAL, Charenton-le-Pont (FR)

(72) Inventors: Daniel Spiegel, Singapore (SG); Guillaume Giraudet, Orleans (FR)

(73) Assignee: Essilor International, Charenton-le-Pont (FR)

( * ) Notice: Subject to any disclaimer, the term of this patent is extended or adjusted under 35 U.S.C. 154(b) by 115 days.

(21) Appl. No.: 18/698,287

(22) PCT Filed: Nov. 17, 2022

(86) PCT No.: PCT/EP2022/082214
§ 371 (c)(1),
(2) Date: Apr. 3, 2024

(87) PCT Pub. No.: WO2023/099223
PCT Pub. Date: Jun. 8, 2023

(65) Prior Publication Data
US 2024/0412327 A1 Dec. 12, 2024

(30) Foreign Application Priority Data
Dec. 2, 2021 (EP) .................................... 21306689

(51) Int. Cl.
*G06T 5/20* (2006.01)
*A61N 5/06* (2006.01)
(Continued)

(52) U.S. Cl.
CPC .............. *G06T 5/20* (2013.01); *A61N 5/0622* (2013.01); *G02B 27/0172* (2013.01); *G06T 5/10* (2013.01);
(Continued)

(58) Field of Classification Search
None
See application file for complete search history.

(56) References Cited

U.S. PATENT DOCUMENTS 4,446,484 A * 5/1984 Powell ...................... G06T 5/20
348/625
5,719,784 A * 2/1998 Clark ................. G01N 33/4833
702/77
(Continued)

FOREIGN PATENT DOCUMENTS

WO 2020141375 A1 7/2020

OTHER PUBLICATIONS

International Search Report for PCT/EP2022/082214, mailed Feb. 24, 2023, 4 pages.
(Continued)

*Primary Examiner* — Jwalant Amin
(74) *Attorney, Agent, or Firm* — NIXON & VANDERHYE

(57) ABSTRACT

A computer-implemented method, an apparatus, a system and a computer program for controlling a sightedness impairment of a subject, the method comprising the steps of receiving (201) an image to display to the subject, determining (202) a spatial frequency power spectrum of the received image, generating (203) an intermediate image by modifying a slope of the spatial frequency power spectrum of the received image, generating (204) a modified image based on the intermediate image and commanding (205) a display to the subject of the modified image.

15 Claims, 7 Drawing Sheets

(51) Int. Cl.

| | |
|---|---|
| *G02B 27/01* | (2006.01) |
| *G06T 5/10* | (2006.01) |
| *G06T 5/73* | (2024.01) |
| *G06T 11/00* | (2006.01) |
| *G02C 11/00* | (2006.01) |

(52) U.S. Cl.

CPC ................ *G06T 5/73* (2024.01); *G06T 11/00* (2013.01); *A61N 2005/0626* (2013.01); *A61N 2005/0642* (2013.01); *A61N 2005/0648* (2013.01); *G02B 2027/0138* (2013.01); *G02C 11/10* (2013.01); *G02C 2202/24* (2013.01); *G06T 2207/20056* (2013.01)

(56) References Cited

U.S. PATENT DOCUMENTS

| | | | | |
|---|---|---|---|---|
| 2009/0169086 | A1* | 7/2009 | Thoms ...................... | G06T 5/10 382/132 |
| 2012/0163124 | A1* | 6/2012 | Akiyama ........... | G01N 29/2406 367/87 |
| 2015/0374210 | A1* | 12/2015 | Durr ................ | A61B 1/000096 600/111 |
| 2020/0364854 | A1* | 11/2020 | Fedewa ................. | G06T 7/0012 |
| 2021/0356767 | A1 | 11/2021 | Kubota et al. | |
| 2022/0187625 | A1* | 6/2022 | Yam ................... | G02B 27/0093 |
| 2022/0319014 | A1* | 10/2022 | Meitav ................. | G06T 3/4007 |

OTHER PUBLICATIONS

Written Opinion of the ISA for PCT/EP2022/082214, mailed Feb. 24, 2023, 5 pages.

Pablo Sanz Diez et al., "Accommodation responses following contrast adaptation", Vision Research, vol. 170, Mar. 24, 2020, pp. 12-17.

Daniel Ian Flitcroft et al., "The Spatial Frequency Content of Urban and Indoor Environments as a Potential Risk Factor for Myopia Development", Visual Neuroscience, Investigative Ophthalmology & Visual Science, vol. 61, No. 11, Article 42, Sep. 28, 2020, pp. 1-10.

Daniel Ian Flitcroft et al., "IMI-Defining and Classifying Myopia: A Proposed Set of Standards for Clinical and Epidemiologic Studies", Investigative Ophthalmology & Visual Science, Special Issue, vol. 60, No. 3, Feb. 2019, pp. M20-M30.

* cited by examiner

[Fig. 1]
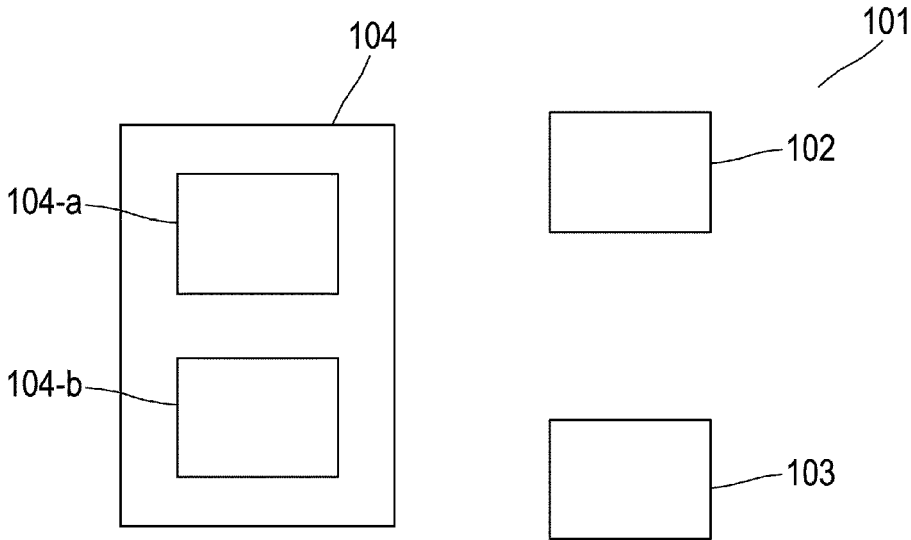
[Fig. 2]
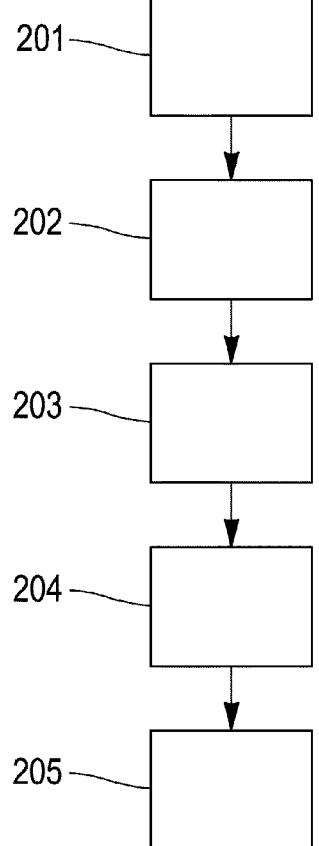

[Fig. 3a]
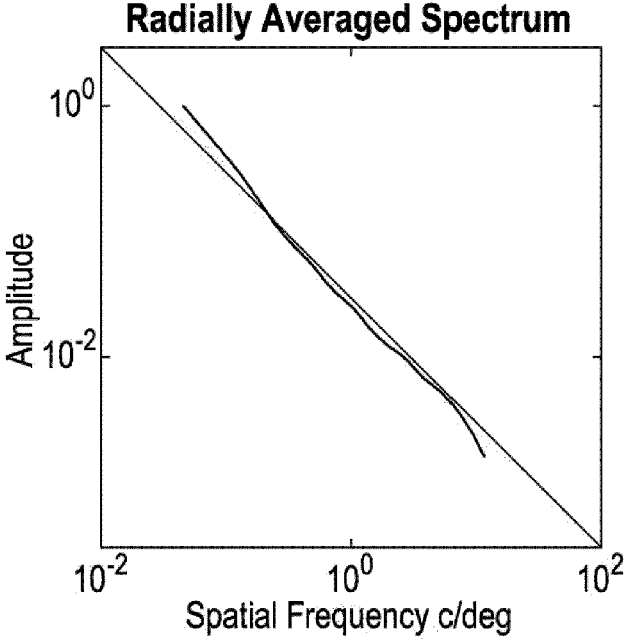
[Fig. 3b]
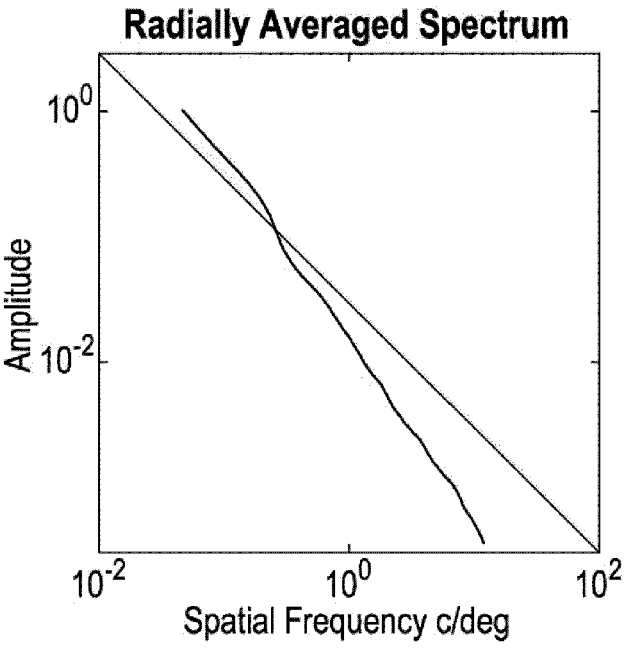

[Fig. 4a]
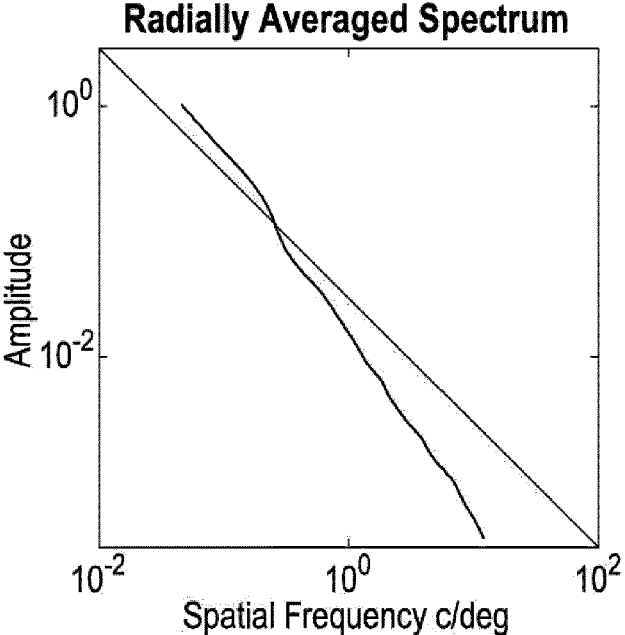
[Fig. 4b]
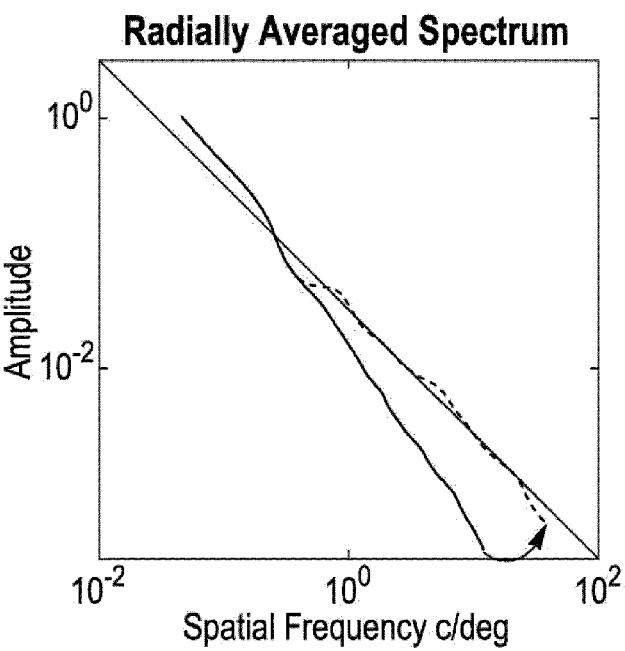

[Fig. 4c]
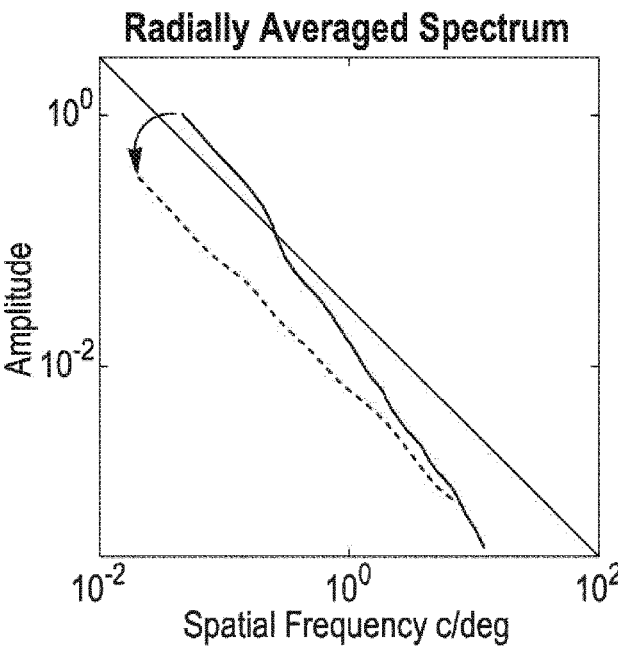

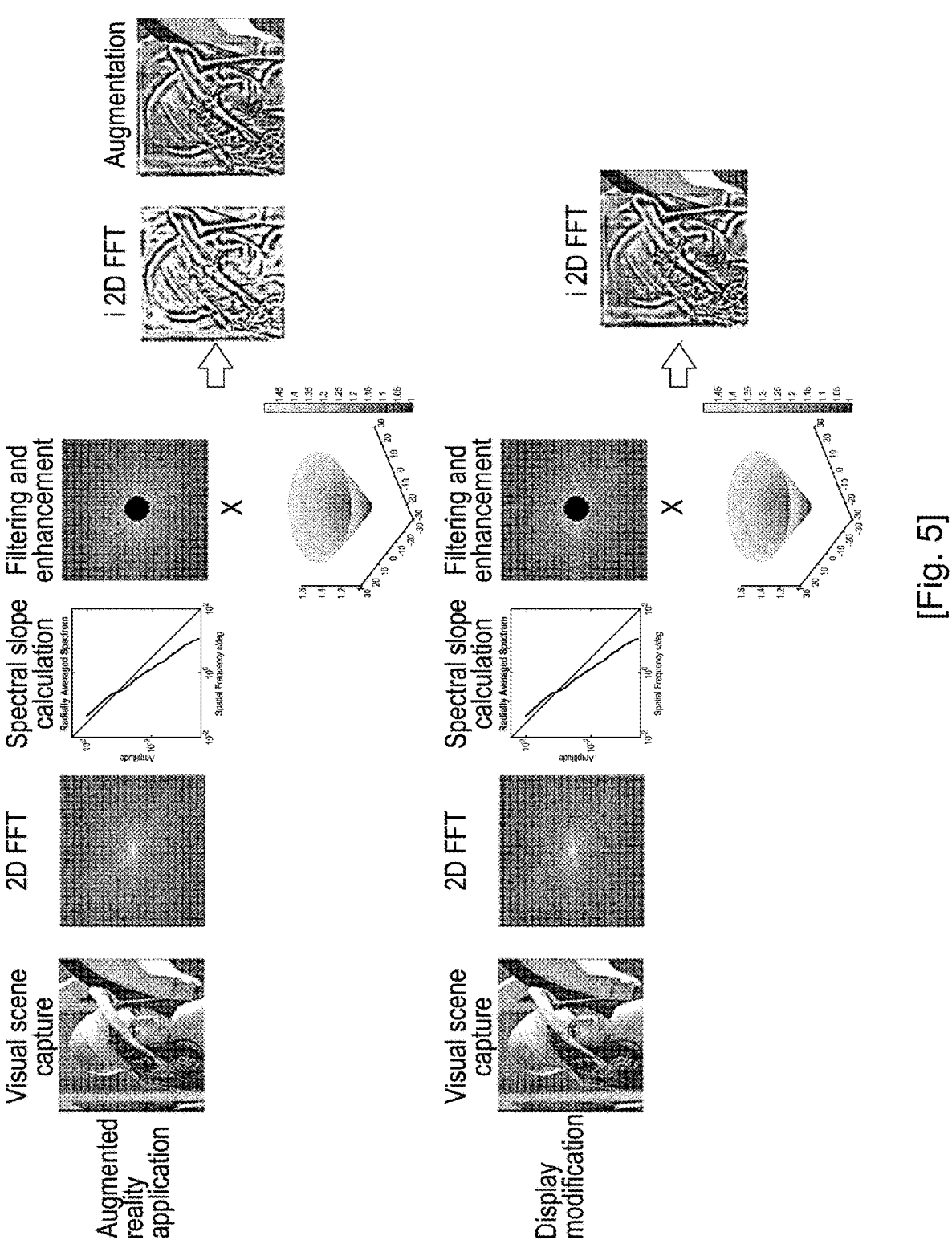
[Fig. 5]

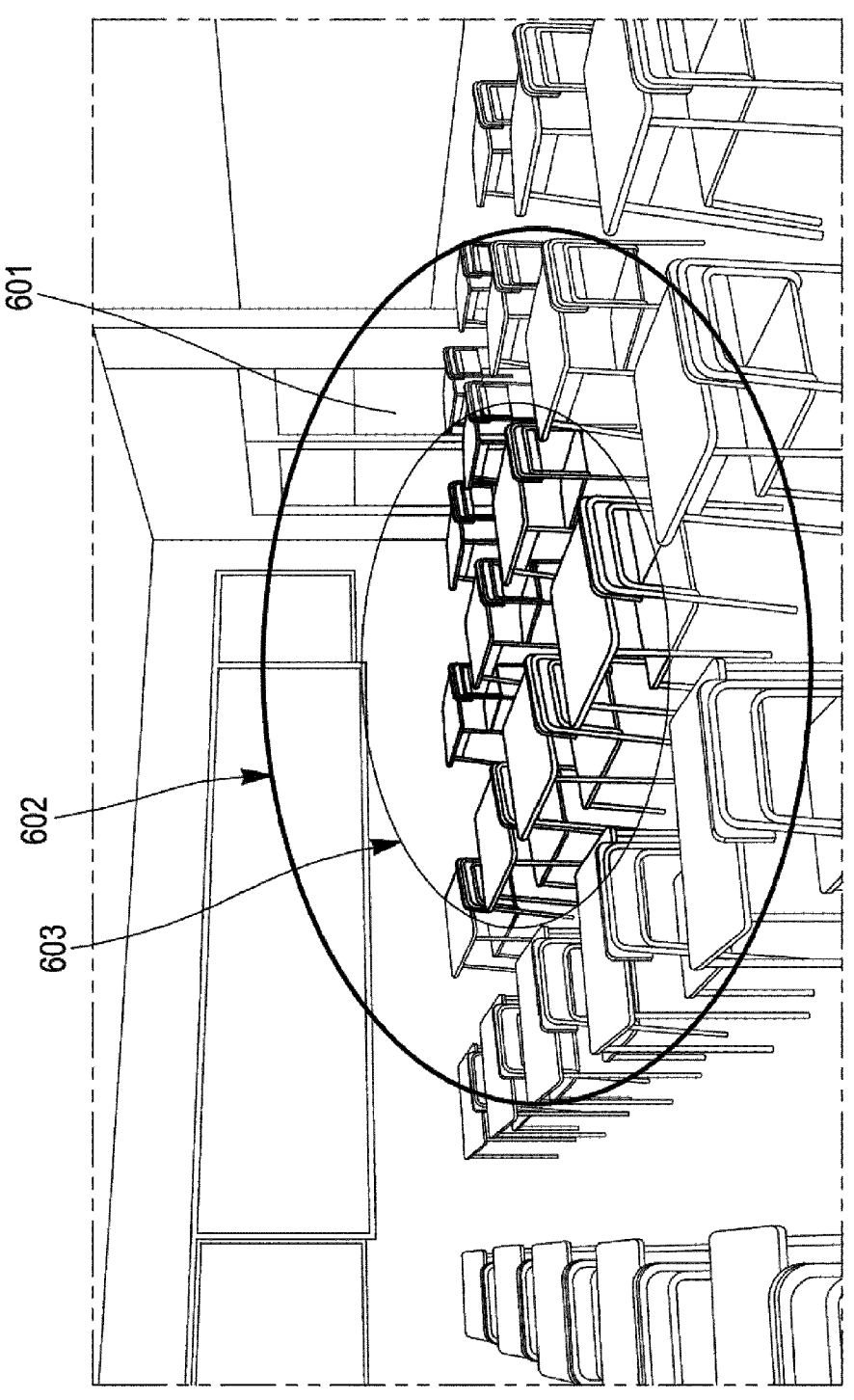
[Fig. 6]

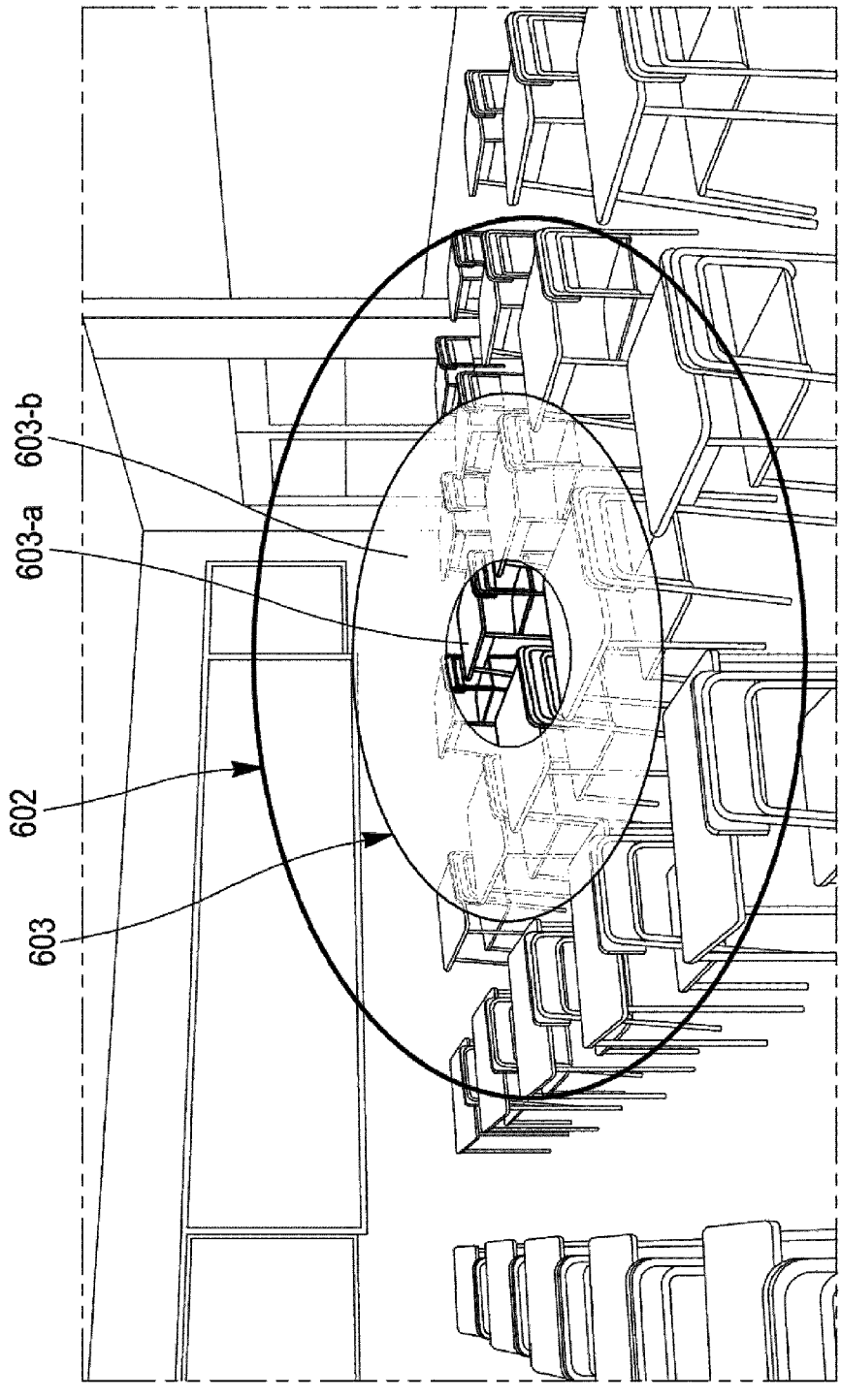
[Fig. 7]

COMPUTER-IMPLEMENTED METHOD, APPARATUS, SYSTEM AND COMPUTER PROGRAM FOR CONTROLLING A SIGHTEDNESS IMPAIRMENT OF A SUBJECT

CROSS-REFERENCE TO RELATED APPLICATIONS

This application is the U.S. national phase of International Application No. PCT/EP2022/082214 filed Nov. 17, 2022, which designated the U.S. and claims priority to EP 21306689.7 filed Dec. 2, 2021, the entire contents of each of which are hereby incorporated by reference.

FIELD

Various aspects of this disclosure generally relate to the field of controlling a sightedness impairment of a subject or user, for example a child or an adult. More precisely this disclosure relates to the control of myopia in the subject.

BACKGROUND

Myopia is one of the most common ocular disorders worldwide and its multifactorial nature makes its control very challenging. Thus, addressing as many aspects of myopia as possible, either alone or in combination, increases the chances of successful myopia control.

In this disclosure the expression myopia control means three different aspects:

Myopia control "as such": any means to or actions of slowing or stopping the progression of myopia. Applies to myopic subjects.

Myopia prevention: Applies to emmetropic or slightly hyperopic subjects. Any means or actions to prevent the subject from becoming myopic, i.e., action of keeping the subject emmetropic or slightly hyperopic.

Myopia delay: any means or actions to delay myopia onset. Applies to pre-myopic subjects. The pre-myopic conditions are described in the article "Defining and Classifying Myopia: A Proposed Set of Standards for Clinical and Epidemiological Studies" published in Investigative Ophthalmology & Visual Science February 2019, Vol.60, M20-M30.

Many solutions exist for myopia control including ophthalmic lenses, eye drops, eye training, etc. However, these traditional solutions have some drawbacks.

There is a need for a new type of devices and methods to realize myopia control.

SUMMARY

The following presents a simplified summary in order to provide a basic understanding of various aspects of this disclosure. This summary is not an extensive overview of all contemplated aspects, and is intended to neither identify key or critical elements of all aspects nor delineate the scope of any or all aspects. The sole purpose is to present some concepts of one or more aspects in a simplified form as a prelude to the more detailed description that is presented later.

One aspect of this disclosure is a computer-implemented method for controlling a sightedness impairment of a subject, the method comprising the steps of receiving an image to display to the subject, determining a spatial frequency power spectrum of the received image, generating a inter-mediate image by modifying a slope of the spatial frequency power spectrum of the received image, generating a modified image based on the intermediate image and commanding a display to the subject of the modified image.

In an embodiment, the computer-implemented method also comprises a step of receiving a value of at least one physiological parameter of the subject and the step of generating the intermediate image is adapted according to the value.

One other aspect of this disclosure is an apparatus for controlling a sightedness impairment of a subject comprising a memory; and at least one processor coupled to the memory and configured to receive an image to display to the subject, determine a spatial frequency power spectrum of the received image, generate an intermediate image by modifying a slope of the spatial frequency power spectrum of the received image, generate a modified image based on the intermediate image and, command a display to the subject of the modified image.

One other aspect of this disclosure is a system for controlling a sightedness impairment of a subject, the system comprising the apparatus, at least one camera configured to receive the image to display to the subject and at least one screen configured to display the modified image.

One other aspect of this disclosure is a computer program for controlling a sightedness impairment of a subject, the computer program comprises instructions which, when the computer program is executed by a calculation module, cause the calculation module to carry out steps of receiving an image to display to the subject, determining a spatial frequency power spectrum of the received image, generating an intermediate image by modifying a slope of the spatial frequency, generating a modified image based on the intermediate image and commanding a display to the subject of the modified image.

DESCRIPTION OF THE DRAWINGS

For a more complete understanding of the description provided herein and the advantages thereof, reference is now made to the brief descriptions below, taken in connection with the accompanying drawings and detailed description, wherein like reference numerals represent like parts.

FIG. 1 represents the system.

FIG. 2 represents the method for controlling the sightedness impairment of the subject.

FIG. 3-a represents the slope of the spatial frequency spectrum of an image of an outdoor environment and FIG. 3-b represents the slope of the spatial frequency spectrum of an image of an indoor environment.

FIGS. 4-a to 4-c represent the effect of the embodiments on the spatial frequency spectrum of the images displayed to the subject.

FIG. 5 represents the method for controlling the sightedness impairment of the subject.

FIG. 6 represents in a first way what the subject sees using the augmented reality headset.

FIG. 7 represents in a second way what the subject sees using the augmented reality headset.

DETAILED DESCRIPTION OF EMBODIMENTS

The detailed description set forth below in connection with the appended drawings is intended as a description of various possible embodiments and is not intended to represent the only embodiments in which the concepts described herein may be practiced. The detailed description includes specific details for the purpose of providing a thorough understanding of various concepts. However, it will be apparent to those skilled in the art that these concepts may be practiced without these specific details. In some instances, well-known structures and components are shown in block diagram form in order to avoid obscuring such concepts.

FIG. 1 represents a system 101 for controlling a sightedness impairment of the subject. This system 101 comprises a camera 102, a screen 103 and an apparatus 104 for example a calculation module 104. The calculation module 104 comprises a memory 104-*a* and a processor 104-*b*.

In an embodiment the system 101 controls a myopia of the subject.

The calculation module 104 is for example a computer, a mobile device or phone or an electrical device.

The camera 102 is for example a front camera configured to capture images in the subject's visual field of view, for example along a gaze axis of the subject. The screen 103 is configured to display images to the subject.

Examples of processors 104-*b* include microprocessors, microcontrollers, graphics processing units (GPUs), central processing units (CPUs), application processors, digital signal processors (DSPs), reduced instruction set computing (RISC) processors, systems on a chip (SoC), baseband processors, field programmable gate arrays (FPGAs), programmable logic devices (PLDs), state machines, gated logic, discrete hardware circuits, and other suitable hardware configured to perform the various functionality described throughout this disclosure.

The memory 104-*a* is computer-readable media. By way of example, and not limitation, such computer-readable media may include a random-access memory (RAM), a read-only memory (ROM), an electrically erasable programmable ROM (EEPROM), optical disk storage, magnetic disk storage, other magnetic storage devices, combinations of the aforementioned types of computer-readable media, or any other medium that can be used to store computer executable code in the form of instructions or data structures that can be accessed by the calculation module 104.

In an embodiment the system 101 comprises two cameras 102 and two screens 103. One of the cameras 102 is configured to capture images along a gaze axis of the right eye of the subject and the other camera 102 is configured to capture images along a gaze axis of the left eye of the subject. One of the screens 103 is configured to display images to the right eye and the other screen 103 is configured to display images to the left eye. In other words a first camera and a first screen are associated with the first eye of the subject and a second camera and a second screen are associated with a second eye of the subject.

Systems 101 can comprise an eyewear for example conventional glasses, smart glasses, a virtual reality headset or an augmented reality headset. The virtual reality headset, the augmented reality headset or the eyewear comprises the camera(s) 102 and the screen(s) 103. The virtual reality or augmented reality headsets are also known as virtual reality or augmented reality glasses. The virtual reality headset or the augmented reality headset can also comprise the calculation module 104. A virtual reality headset is a head-mounted device that displays images to the wearer and in which all of the visual information is digital and provided by the screens, without any access to the real world outside. An augmented reality headset is also a head-mounted device that displays images to the wearer; however, it provides a mix between the digital screen/display and the real world, therefore the augmented reality device must comprise a see-through technology. In other words, virtual reality is a computer-generated simulation of a three-dimensional image or environment that can be interacted with in a seemingly real or physical way by a person using special electronic equipment, such as a helmet with a screen inside or gloves fitted with sensors. Augmented reality is a technology that superimposes a computer-generated image on a user's view of the real world, thus providing a composite view.

Different central and peripheral adjustments of the spatial frequency spectrum of the scenes may be proposed at different stages of myopia progression or risk of myopia progression. For instance, we may rebalance the low and high spatial frequencies on the whole visual field for myopia prevention, following the principles described earlier, i.e. by either boosting the High Spectral Frequencies (HSF) or lowering the low spectral frequencies, and make indoor scenes statistics match or become closer to outdoor scenes statistics. After myopia onset, for slowing down its progression, peripheral and central image processing may be distinguished with a rebalancing of the spectral frequencies in the center and a contrast reduction in the High Spectral Frequencies in the peripheral field. The contrast reduction in the peripheral field is also known as low-pass filtering.

The memory 104-*a* is configured to store a computer program comprising instructions which, when the program is executed by the processor 104-*b*, cause the calculation module 104 or the system 101 to realize a method for controlling the myopia of the subject. This method, presented FIG. 2, comprises the steps of:

receiving 201 an image to display to the subject, determining 202 a spatial frequency power spectrum of the received image, generating 203 an intermediate image by modifying a slope of the spatial frequency power spectrum of the received image and, generating 204 a modified image based on the intermediate image command 205 a display to the subject of the modified image.

The spatial frequency power spectrum of an image is the distribution of power into frequency components composing that image.

To obtain the slope we can average the spatial frequency power spectrum to generate a single amplitude spectrum representing the average of each directional meridian within the image. We can then use linear regression to calculate the slope of the relationship between log amplitude and log spatial frequency.

The step of generating 203 the intermediate image comprises a step of comparing the slope of the spatial frequency power spectrum with a threshold and when the slope is above the threshold a step of decreasing the slope and/or, when the slope is below the threshold a step of increasing the slope.

In an embodiment the slope is taken on a log-log representation of the power associated with the spatial frequency components.

The threshold is between −1.2 and −0.8, advantageously between −1.1 and −0.9 for example −1.

The modified image can be the intermediate image or a difference between the intermediate image and the received image.

In an embodiment the method of FIG. 2 comprises a step of receiving a value of at least one physiological parameter of the subject. The physiological parameters can be indications of myopia risk factors, for example central and peripheral eye length, central and peripheral refraction of the eye, eye aberrations, an indication of myopia in the ascendants or descendants of the subject, an amount of near work, genetic profile, etc. The step of generating 203 is adapted according to the value. For example the threshold can also be adjusted according to this value.

Spending time outdoors is effective to control myopia. One of the factors may be the higher content of high spatial frequency information in the outdoor (natural) visual environment compared to indoor and/or man-made visual environment.

Natural (opposite of man-made) visual environment is characterized by a spatial frequency spectrum (obtained by Fourier analysis), whereby the amplitude spectrum (also referred as to spectral power or spatial frequency contrast) linearly decreases with increasing spatial frequency with a slope close to −1.0 when plotted on a log-log scale. The FIG. 3-a represents the slope of the spatial frequency spectrum of an image of an outdoor environment and the FIG. 3-b represents the slope of the spatial frequency spectrum of an image of an indoor environment. In the FIG. 3-a, the slope of the spatial frequency spectrum is about −1. In the FIG. 3-b, the slope of the spatial frequency spectrum is about −1.4. As presented in FIG. 3-b indoor and man-made environment exhibits a reduced power at high spatial frequencies that after Fourier analysis results in a steeper slope of the spatial frequency spectrum, i.e. often slope <−1.

Using the embodiments of this disclosure, it is possible to employ image processing algorithms that calculate in real-time the spatial frequency spectrum of an image of a visual scene and, if the power spectrum slope falls under a specified threshold, enhances the visual scene by increasing the power of the high spatial frequencies or decreasing the power of the low spatial frequencies. This allows the generation of an image with the spatial frequency power spectrum closer to the one of the images of an outdoor or natural environment, i.e. slope ~−1.0. The FIGS. 4-a to 4-c represent the effect of the embodiments on the spatial frequency spectrum of the images displayed to the subject. The FIG. 4-a represents the slope of the spatial frequency spectrum of the received image. The FIG. 4-b represents the increase of the power of the high spatial frequencies. In FIG. 4-b, the slope representing with a dashed line is the slope with the increase of the power of the high spatial frequencies. The FIG. 4-c represents the decrease of the power of the low and/or mid spatial frequencies. In FIG. 4-c, the slope representing with a dashed line is the slope with the decrease of the power of the low and/or mid spatial frequencies.

The step of increasing the slope can comprise a step of filtering the received image using a high-pass 2D filter and/or the step of decreasing the slope can comprise a step of filtering the received image using a low-pass 2D filter.

The step of increasing the slope can otherwise comprise:
applying a discrete Fourier transform to the received image and
decreasing power of low or mid spatial frequencies of the discrete Fourier transform of the received image to obtain an intermediate image, or
increasing power of high spatial frequencies of the discrete Fourier transform of the received image to obtain the intermediate image, and
applying an inverse discrete Fourier transform to the intermediate image To increase the slope, the method can also combine the increase of the power of the high spatial frequencies and the decrease of the power of the low mid spatial frequencies.

The step of decreasing the slope can otherwise comprise:
applying a discrete Fourier transform to the received image and
increasing power of low or mid spatial frequencies of the discrete Fourier transform of the received image to obtain an intermediate image, or
decreasing power of high spatial frequencies of the discrete Fourier transform of the received image to obtain the intermediate image and
applying an inverse discrete Fourier transform to the intermediate image.

To decrease the slope, the method can also combine the decrease of the power of the high spatial frequencies and the increase of the power of the low mid spatial frequencies.

The high frequencies are frequencies above 10 cycles per degree (cpd).

Cycles per degree is a unit of spatial frequency. It is equal to the number of cycles of a grating (one dark and one light band) that subtends an angle of one degree at the eye.

The mid frequencies are frequencies between 3 and 10 cpd

The low frequencies are frequencies below 3 cpd

In other words the increase of power of the high spatial frequencies may be achieved by implementing the following image processing pipeline represented in FIG. 5. The slope/amount of the power increase is calculated so the compound spectrum (i.e. original visual scene+the visual stimuli augmenting the original visual scene) follows −1 slope.

As presented in FIG. 5 the method for controlling a myopia of the subject comprises the following steps:
Receiving an image of the visual scene
Transforming the image using a 2D Fourier transform
Calculating the log-log slope of the spectral power of the transformed image
Filtering of the transformed image to realize a 2D selective increase of the frequency domain using, for example, a funnel-shaped function for example a 2D Gaussian function. The lower end of the spatial frequency range (no boost) corresponds, for example to, 0.1 cycles per degree (cpd); and the higher end of the spatial frequency range (maximal boost) is for example 30 cpd,
Transforming, using a 2D inverse Fourier, the filtered image to obtain the intermediate image,
Generating the modified image based on the intermediate image, the modified image can be the intermediate image or can be the difference between the intermediate image and the received image,
Display the modified image to the subject, the modified image can be overlaid over the visual scene (i.e., the visual scene is augmented by the filtered and boosted image).

In another embodiment, the step of generating 204 the intermediate image comprises the generation of an intermediate image that when visually combined with the real visual scene would create a compound image having a spectral power of slope of −1. In this case the modified image displayed to the subject is the intermediate image. In other word the method as presented in FIG. 5 comprises the following steps:
Receiving an image of the visual scene
Transforming the image using a 2D Fourier transform
Calculating the log-log slope of the spectral power of the transformed image
Constructing an overlay image that when combined with the visual scene would create a compound image having a slope of −1, such an image may consist, for example, of filtered noise or (random) geometrical shapes.

Display the final image to the subject, the final image can be overlaid over the visual scene (i.e., the visual scene is augmented by the filtered and boosted image).

This embodiment allows the generation of a random image whose spatial frequency spectral power is identical to the overlay/boost image. This embodiment does not require precise alignment between the original image and the modified image. The modified image would be spatially decorrelated from the received image and the visual scene and thus would not need spatial alignment. This is particularly advantageous when using augmented reality headsets.

The method can also comprise a decrease of the spatial frequency content for low or mid spatial frequencies, instead of or in addition to increasing the high spatial frequencies. The decrease in the spatial frequency content can be achieved by a usage of a 2D selective decrease of the frequency domain using, for example but not limited to, a funnel-shaped function. The lower end of the spatial frequency range (maximal reduction) corresponds for example to 0.1 cycles per degree (cpd); and the higher end of the spatial frequency range (no reduction or augmentation) is for example 30 cpd. The decrease at the trough of the function should be calculated so the compound spectrum (i.e. original visual scene+the visual stimuli augmenting the original visual scene) follows −1 slope.

In other words, the method of this disclosure dynamically alters images of real life visual scenes and displays these altered images on the screen. When using a virtual reality headset only the altered images are seen by the subject, therefore in this case the modified image is generally the intermediate image. When using an augmented reality headset the real scene is seen through the screen displaying the altered images. In this case the altered images are generally the difference between the intermediate image and the received image. The method modifies dynamically specific spatial frequency content of the image in order to ensure that the power spectrum of the image displayed follows a slope of −1. This method allows the limitation of the eye growth, the increase of the visual comfort and/or the decrease of the visual fatigue. The method calculates (preferable in real-time) the spatial frequency power spectrum and its slope and augments the power of a specific range of spatial frequencies of the image in order to bring the compound (i.e. original visual scene+the visual stimuli augmenting the original visual scene) power spectrum slope closer to −1. In case of man-made environments, this range is at the higher end of the spectrum.

The method described above can be performed either over the entire visual field or in a specific sub-region, for example in the central visual field. This method can be complemented by other visual image manipulations, for example an enhancement of the high spatial frequencies in the centre of the visual field can be complemented by a decrease of high spatial frequencies in the periphery of the visual field.

The magnitude of image augmentation/modification within each sub-region can be uniform or can follow a specific function. For example, the high spatial frequency enhancement can be strongest in the centre of the enhancement zone. Similarly, the low spatial frequency decrease may be strongest in the periphery of the reduction zone.

The transition between the sub-region may be abrupt or follow a blending function, for example a sigmoid function.

The system can comprise an eye tracker configured to determine the gaze axis and to use this gaze axis to determine the center of the visual field and the periphery of the visual field.

In an embodiment the system 101 is configured to calculate the spatial frequency power spectrum of the received images and if the slope of the spatial frequency power spectrum is under a threshold of activation (for example if the slope is below −1.4 preferable below −1.3) the method of FIG. 2 is realized by the system 101.

The FIG. 6 represents in a first way what the subject sees using the augmented reality headset. The global external shape 601 depicts the binocular field of view of the subject through the augmented reality headset, limited by the frame 602 of the augmented reality headset. The inner part 603 depicts the augmented reality field where images received from the front camera are modified using the method of FIG. 2 to increase, preferably in real-time, the power of high spectral frequencies of the received image and superimpose this modified image on the real world environment.

The FIG. 7 represents in a second way what the subject sees using the augmented reality headset. As illustrated in FIG. 7 the received image comprises two parts. A first part 603-*a* is a central part of the received image. A second part 603-*b* is a part of the received image located at the periphery of the first part 603-*b*. In this embodiment only the first part 603-*a* is modified using the previously presented method. The second part 603-*b* is degraded using, for example, a low-pass filter. The modified image comprising the first part 603-*a* and the second part 603-*b* is superimposed on the real world environment.

The augmented reality headset can also comprise one lens or two lenses configured to optically modify a view at a periphery of the image to display to the subject. The lens can be configured to provide, in the peripheral field, an optical microstructure having an optical function of not focusing an image on the retina of the eye of the wearer so as to slow down the progression of the abnormal refraction of the eye of the subject. In case of two lenses one of the lenses is associated with one of the eyes of the subject and the other lens is associated with the other eye of the subject.

In other words the modifications of the image using the previously presented method can be only induced in a certain portion of the field of view of the subject, for example, only in the central visual field. This modification of the central part of the field of view of the subject can also be combined with other local alterations of spatial frequency spectra of the visual scene, for example reduction of high spatial frequencies in the peripheral part of the center of the field of view. This embodiment advantageously allows a better control of the myopia progression of the subject.

The method described in this disclosure can be used to modify the image displayed in the central vision field only in a zone extending at less than 10° around the gaze axis of the eye. The passive (optical) modification of the view in the periphery of this central vision field can be achieved with either microlenses array or diffusion dots. This embodiment is particularly advantageous to slow down myopia progression.

To ensure that the filtered image has the same luminance as the source image, a luminance matching algorithm can be employed. For example, the intensity of each pixel in the luminance-matched filtered image ($pixLum_{match}$) can be calculated using the following equation: $pixLum_{match}=(pixLum_{unMatch}-M_{unMatch})/S_{unMatch}*S_{source}+M_{source}$; where $pixLum_{unMatch}$ is the intensity of the corresponding pixel in the output image before luminance matching, $M_{unMatch}$ is the mean of the pixel intensities of the output image before luminance matching, $S_{unMatch}$ is the standard deviation of the pixel intensities of the output image before luminance matching, $S_{source}$ is the standard deviation of the pixel intensities of the source image, and $M_{source}$ is the mean of the pixel intensities of the source image.

The method can work in real time, e.g. in case of streaming, watching TV, gaming etc. In the case of playing stored content (i.e. movie from the hard drive or DVD), the method may be realized prior to playing.

The invention claimed is:

1. Computer-implemented method for controlling a sightedness impairment of a subject, the method comprising the steps of:

receiving an image to display to the subject, determining a spatial frequency power spectrum of the received image, determining a slope of the spatial frequency power spectrum of the received image by generating a radially-averaged amplitude spectrum and computing, on log amplitude versus log spatial frequency, a linear-regression slope, generating an intermediate image by modifying the slope of the spatial frequency power spectrum of the received image, generating a modified image based on the intermediate image, and commanding a display to the subject of the modified image, wherein the step of generating the intermediate image comprises:

a step of comparing the slope of the spatial frequency power spectrum with a threshold, when the slope is above the threshold a step of decreasing the slope, and/or when the slope is below the threshold a step of increasing the slope.

2. Computer-implemented method according to claim 1, the modified image being the intermediate image or the modified image being a difference between the intermediate image and the received image.

3. Computer-implemented method according to claim 1, the step of increasing the slope comprising a step of filtering the received image using a high-pass 2D filter.

4. Computer-implemented method according to claim 1, the step of increasing the slope comprising:

applying a discrete Fourier transform to the received image, decreasing power of low or mid spatial frequencies and/or increasing power of high spatial frequencies of the discrete Fourier transform of the received image to obtain an intermediate image, and applying an inverse discrete Fourier transform to the intermediate image.

5. Computer-implemented method according to claim 1, the step of decreasing the slope comprising a step of filtering the received image using a low-pass 2D filter.

6. Computer-implemented method according to claim 1, the step of decreasing the slope comprising:

applying a discrete Fourier transform to the received image, increasing power of low or mid spatial frequencies and/or decreasing power of high spatial frequencies of the discrete Fourier transform of the received image to obtain an intermediate image, and applying an inverse discrete Fourier transform to the intermediate image.

7. Computer-implemented method according to claim 1, the received image comprising a first part and a second part, the step of generating being configured to modify only the first part.

8. Computer-implemented method according to claim 7, the method also comprising a step of modifying the second part, for example by degrading the second part.

9. An apparatus for controlling a sightedness impairment of a subject comprising a memory; and at least one processor coupled to the memory and configured to:

receive an image to display to the subject, determine a spatial frequency power spectrum of the received image, determine a slope of the spatial frequency power spectrum of the received image by generating a radially-averaged amplitude spectrum and compute, on log amplitude versus log spatial frequency, a linear-regression slope, generate an intermediate image by modifying a slope of the spatial frequency power spectrum of the received image, generate a modified image based on the intermediate image, and command a display to the subject of the modified image, wherein for generating the intermediate image the apparatus is also configured to:

compare the slope of the spatial frequency power spectrum with a threshold, when the slope is above the threshold the apparatus is also configured to decrease the slope, and/or when the slope is below the threshold the apparatus is also configured to increase the slope.

10. A system for controlling a sightedness impairment of a subject, the system comprising the apparatus of claim 9, a camera configured to receive the image to display to the subject and a screen configured to display the modified image.

11. System according to claim 10, also comprising an eyewear comprising the camera and the screen.

12. System according to claim 11, the camera being a first camera and the screen being a first screen, the system comprising a second camera and a second screen, the eyewear comprising the second camera and the second screen, the first camera and the first screen being associated to a first eye of the subject and the second camera and the second screen being associated to a second eye of the subject.

13. System according to claim 11, the eyewear being an augmented reality headset, the augmented reality headset comprising a lens, the lens being configured to modify a view at a periphery of the image to display to the subject.

14. Eyewear comprising an apparatus for controlling a sightedness impairment of a subject, a camera and a screen, the apparatus comprising a memory; and at least one processor coupled to the memory and configured to:

receive an image to display to the subject, determine a spatial frequency power spectrum of the received image, determine a slope of the spatial frequency power spectrum of the received image by generating a radially-averaged amplitude spectrum and compute, on log amplitude versus log spatial frequency, a linear-regression slope, generate an intermediate image by modifying a slope of the spatial frequency power spectrum of the received image, generate a modified image based on the intermediate image, and command a display to the subject of the modified image, wherein for generating the intermediate image the apparatus is also configured to:

compare the slope of the spatial frequency power spectrum with a threshold, when the slope is above the threshold the apparatus is also configured to decrease the slope, and/or when the slope is below the threshold the apparatus is also configured to increase the slope, the camera being configured to receive the image to display to the subject and the screen being configured to display the modified image.

15. A non-transitory computer-readable storage medium storing instructions that, when executed by one or more processors of a calculation module, cause the calculation module to perform steps of:

receiving an image to display to the subject, determining a spatial frequency power spectrum of the received image, determining a slope of the spatial frequency power spectrum of the received image by generating a radially-averaged amplitude spectrum and computing, on log amplitude versus log spatial frequency, a linear-regression slope, generating an intermediate image by modifying a slope of the spatial frequency, generating a modified image based on the intermediate image, and commanding a display to the subject of the modified image, wherein the step of generating the intermediate image comprises:

a step of comparing the slope of the spatial frequency power spectrum with a threshold, when the slope is above the threshold a step of decreasing the slope, and/or when the slope is below the threshold a step of increasing the slope.

* * * * *